United States Patent
O'Malley (10) Patent No.: US 11,564,878 B2
(45) Date of Patent: Jan. 31, 2023

(54) ORAL CARE PRODUCT FORMULATION

(71) Applicant: Paul O'Malley, Sylmar, CA (US)

(72) Inventor: Paul O'Malley, Sylmar, CA (US)

(*) Notice: Subject to any disclaimer, the term of this patent is extended or adjusted under 35 U.S.C. 154(b) by 52 days.

(21) Appl. No.: 17/303,780

(22) Filed: Jun. 7, 2021

(65) Prior Publication Data
US 2021/0378945 A1 Dec. 9, 2021

Related U.S. Application Data

(60) Provisional application No. 63/202,307, filed on Jun. 4, 2021, provisional application No. 63/036,300, filed on Jun. 8, 2020.

(51) Int. Cl.
| | |
|---|---|
| *A61K 8/9789* | (2017.01) |
| *A61K 8/34* | (2006.01) |
| *A61K 8/25* | (2006.01) |
| *A61K 8/24* | (2006.01) |
| *A61K 8/99* | (2017.01) |

(Continued)

(52) U.S. Cl.
CPC .......... *A61K 8/9789* (2017.08); *A61K 8/19* (2013.01); *A61K 8/24* (2013.01); *A61K 8/25* (2013.01); *A61K 8/26* (2013.01); *A61K 8/27* (2013.01); *A61K 8/345* (2013.01); *A61K 8/362* (2013.01); *A61K 8/37* (2013.01); *A61K 8/58* (2013.01); *A61K 8/604* (2013.01); *A61K 8/676* (2013.01); *A61K 8/678* (2013.01); *A61K 8/731* (2013.01); *A61K 8/9794* (2017.08); *A61K 8/99* (2013.01);

(Continued)

(58) Field of Classification Search
CPC .......... A61K 8/0241; A61K 8/19; A61K 8/24; A61K 8/25; A61K 8/26; A61K 8/27; A61K 8/345; A61K 8/362; A61K 8/365; A61K 8/37; A61K 8/44; A61K 8/58; A61K 8/602; A61K 8/604; A61K 8/676; A61K 8/678; A61K 8/731; A61K 8/922; A61K 8/965; A61K 8/9789; A61K 8/9794; A61K 8/99; A61K 2035/115; A61K 2300/00; A61K 2800/413; A61Q 11/00

See application file for complete search history.

(56) References Cited

U.S. PATENT DOCUMENTS

| | | | | |
|---|---|---|---|---|
| 9,403,181 | B2 * | 8/2016 | O'Malley | A61K 33/30 |
| 9,554,973 | B2 * | 1/2017 | O'Malley | A61K 8/19 |
| 9,603,791 | B2 * | 3/2017 | O'Malley | A61K 8/345 |

OTHER PUBLICATIONS

Ronald Lindahl, Aldehyde Dehydrogenases and Their Role in Carcinogenesis, Critical Reviews in Biochemistry and Molecular Biology, 1992, 27:4-5, 283-335, DOI: 10.3109/10409239209082565.

(Continued)

*Primary Examiner* — Isaac Shomer
*Assistant Examiner* — Amanda Michelle Petritsch
(74) *Attorney, Agent, or Firm* — Hackler Daghighian Martino & Novak (57) ABSTRACT

A three-part method of cleaning a user's teeth and/or gums is disclosed. First, a user applies a tonic of essential oils to the user's teeth and/or gums by either brushing, rubbing, rinsing and/or flossing with the tonic thereby destroying harmful bacteria. Second, the user brushes with a toothpaste having nano-hydroxyapatite being particles of 50 nanometers or smaller. The nano-hydroxyapatite is absorbed into the surface opening inside dentinal tubules of the teeth. Third, the user seeds their mouth with an oral probiotic having beneficial bacteria. The third step must come after both the first and second steps.

19 Claims, 2 Drawing Sheets

(51) Int. Cl.
*A61K 8/27* (2006.01)
*A61K 8/19* (2006.01)
*A61K 8/362* (2006.01)
*A61K 8/67* (2006.01)
*A61K 8/58* (2006.01)
*A61K 8/26* (2006.01)
*A61K 8/73* (2006.01)
*A61K 8/37* (2006.01)
*A61K 8/60* (2006.01)
*A61Q 11/00* (2006.01)
*A61K 8/9794* (2017.01)
*A61K 35/00* (2006.01)

(52) U.S. Cl.
CPC ........ *A61Q 11/00* (2013.01); *A61K 2035/115* (2013.01); *A61K 2300/00* (2013.01)

(56) References Cited

OTHER PUBLICATIONS

Adriana Simionatto Guinesi, Carolina Andolfatto, Idomeo Bonetti-Filho and Arnaldo Cardoso; Ozonized Oils: A qualitative and quantitative analysis; Jan. 2011 Brazilian Dental Journal 22(1):37-40, DOI:10.1590/S0103-64402011000100006. (https://www.researchgate.net/publication/51076588_Ozonized_Oils_A_qualitative_and_quantitative_analysis).

Murilo Baena Lopes, Mário Alexandre Coelho Sinhoreti and Alcides Gonini Júnior; Comparative study of tubular diameter and quantity for human and bovine dentin at different depths; Jan. 2009, Brazilian Dental Journal 20(4):279-83, DOI:10.1590/S0103-64402009000400003.

Monika Supová; Isolation and Preparation of Nanoscale Bioapatites from Natural Sources: A Review; Apr. 2014, Journal of Nanoscience and Nanotechnology 14(1):546-63, DOI:10.1166/jnn.2014.8895. (https://pubmed.ncbi.nlm.nih.gov/24730282/).

* cited by examiner

ORAL CARE PRODUCT FORMULATION

CROSS-REFERENCE TO RELATED APPLICATIONS

This non-provisional application claims priority to provisional application 63/036,300 filed on Jun. 8, 2020 and to provisional application 63/202,307 filed on Jun. 4, 2021, the entire contents of which being both applications are fully incorporated herein with these references.

DESCRIPTION

Field of the Invention

The present invention generally relates to oral care. More particularly, the present invention relates to a three-part method of cleaning a user's teeth and/or gums by removing harmful bacteria and then seeding in beneficial bacteria.

Background of the Invention

This is an improvement upon the following U.S. Pat. No. 9,403,181 issued Aug. 2, 2016; U.S. Pat. No. 9,554,973 issued on Jan. 31, 2017; and U.S. Pat. No. 9,603,791 issued on Mar. 28, 2017—the contents of which are fully incorporated herein with these references.

SUMMARY OF THE INVENTION

The present invention teaches a method of cleaning a user's teeth and/or gums, the method comprising the steps of: a) applying a tonic to the user's teeth and/or gums by either brushing, rubbing, rinsing and/or flossing with the tonic, the tonic comprising: tea tree essential oil comprising 0.10-1.0% by mass of the tonic; peppermint and spearmint essential oil comprising 20.0-50.0% by mass of the tonic; almond essential oil comprising 15.0-35.0% by mass of the tonic; b) brushing with a toothpaste, the toothpaste comprising: aloe comprising 5.0-37.0% by mass of the toothpaste; himalayan pink salt comprising 2.0-5.0% by mass of the toothpaste; natural preservative comprising 0.10-2.0% by mass of the toothpaste; citric acid comprising 00.40% by mass of the toothpaste with a variation of plus or minus 20%; xylitol comprising 30.0-50.0% by mass of the toothpaste; ascorbic acid comprising 00.10% by mass of the toothpaste with a variation of plus or minus 20%; baking soda comprising 02.50-10.0% by mass of the toothpaste; zinc gluconate comprising 0.20-2.0% by mass of the toothpaste; zinc citrate comprising 01.00% by mass of the toothpaste with a variation of plus or minus 20%; calcium carbonate comprising 10.00% by mass of the toothpaste with a variation of plus or minus 20%; calcium carbonate in a hydroxyapatite shell comprising 05.00% by mass of the toothpaste with a variation of plus or minus 20%; silicon dioxide comprising 5.0-15.0% by mass of the toothpaste; glycyrrhizic acid 3.0-6.0% by mass of the toothpaste with a variation of plus or minus 20%; nano-hydroxyapatite comprising 6.50-20.0% by mass of the toothpaste, wherein the nano-hydroxyapatite consists essentially of particles of 50 nanometers (0.05 microns) or smaller; sodium bentonite comprising 1.0-3.0% by mass of the toothpaste; vitamin E oil comprising 0.10-3.0% by mass of the toothpaste; tea tree oil comprising 0.10-3.0% by mass of the toothpaste; wintergreen oil comprising 1.0-3.0% by mass of the toothpaste; cellulose gum comprising 1.0-3.0% by mass of the toothpaste; sodium cocoyl glutamate comprising 1.0-4.0% by mass of the toothpaste; c) seeding the user's teeth and gums with an oral probiotic, the oral probiotic being in the form of a tablet, the oral probiotic tablet comprising: i.) *Lactobacillus acidophilus* comprising 15.0% to 40.0% per mass of the oral probiotic; ii.) *Lactobacillus reuteri* comprising 5.0% to 20.0% per mass of the oral probiotic; iii.) *Lactobacillus salivarius* comprising 5.0% to 20.0% per mass of the oral probiotic; iv.) *Lactobacillus paracasei* comprising 5.0% to 20.0% per mass of the oral probiotic; v.) *Streptococcus thermophiles* comprising 5.0% to 20.0% per mass of the oral probiotic; vi.) *Streptococcus salivarius* BLIS K-12 comprising 5.0% to 30.0% per mass of the oral probiotic; vii.) *Streptococcus salivarius* BLIS M-18 comprising 5.0% to 30.0% per mass of the oral probiotic; viii.) zinc oxide comprising 0.2% to 5.0% per mass of the oral probiotic; ix.) hydroxyapatite comprising 0.1% to 25.0% per mass of the oral probiotic; and x.) dicalcium phosphate comprising 0.1% to 5.0% per mass of the oral probiotic; d) wherein step c) must come after both step a) and step b).

In other exemplary embodiments, step a) may be before step b) or step b) may be before step a). Furthermore, step a) and step b) may be combined together, i.e. are accomplished/performed at the same time.

The tonic and/or the toothpaste may have a pH of 7.1 to 7.4. The tonic and/or the toothpaste may be 99.9% by mass free of glycerin.

The present invention also teaches a method of producing a toothpaste, the method comprising the steps of: a) mixing the following ingredients into a first mixture: aloe comprising 5.0-37.0% by mass of the toothpaste; himalayan pink salt comprising 2.0-5.0% by mass of the toothpaste; natural preservative comprising 0.10-2.0% by mass of the toothpaste; citric acid comprising 00.40% by mass of the toothpaste with a variation of plus or minus 20%; xylitol comprising 30.0-50.0% by mass of the toothpaste; ascorbic acid comprising 00.10% by mass of the toothpaste with a variation of plus or minus 20%; b) mixing the first mixture with the following ingredients forming a second mixture: baking soda comprising 02.50-10.0% by mass of the toothpaste; zinc gluconate comprising 0.20-2.0% by mass of the toothpaste; zinc citrate comprising 01.00% by mass of the toothpaste with a variation of plus or minus 20%; calcium carbonate comprising 10.00% by mass of the toothpaste with a variation of plus or minus 20%; calcium carbonate in a hydroxyapatite shell comprising 05.00% by mass of the toothpaste with a variation of plus or minus 20%; silicon dioxide comprising 5.0-15.0% by mass of the toothpaste; glycyrrhizic acid 3.0-6.0% by mass of the toothpaste with a variation of plus or minus 20%; nano-hydroxyapatite comprising 6.50-20.0% by mass of the toothpaste, wherein the nano-hydroxyapatite consists essentially of particles of 50 nanometers (0.05 microns) or smaller; sodium bentonite comprising 1.0-3.0% by mass of the toothpaste; c) mixing the second mixture with the following ingredients forming a third mixture: vitamin E oil comprising 0.10-3.0% by mass of the toothpaste; tea tree oil comprising 0.10-3.0% by mass of the toothpaste; wintergreen oil comprising 1.0-3.0% by mass of the toothpaste; cellulose gum comprising 1.0-3.0% by mass of the toothpaste; d) mixing the third mixture with the following ingredient forming the toothpaste: sodium cocoyl glutamate comprising 1.0-4.0% by mass of the toothpaste.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Since the beginning of the first patent application the inventor has learned quite a bit through research and feedback and has developed now, instead of a dual system, a trio system. This patent application now teaches a trio process of how to: (1) help reduce the number of pathogenic bacteria naturally using essential oils; (2) brush with a toothpaste where the toothpaste will also reduce the bad bacteria using essential oils and proper cleaning but at the same time using hydroxyapatite in its nano form or small particle size introduce positive microscopic re-mineralization of the teeth and any exposed dentin; and (3) put back healthy bacteria with the patented advanced probiotic formula;

When the inventor first released the advanced oral probiotics by Great Oral Health Inc., the inventor realized that the dicalcium phosphate, which is a bulking agent used to hold the capsule or lozenge together, was also instrumental in converting to hydroxyapatite. The inventor discovered that dicalcium phosphate in the presence of saliva or water breaks down basically into hydroxyapatite.

Figure 1:
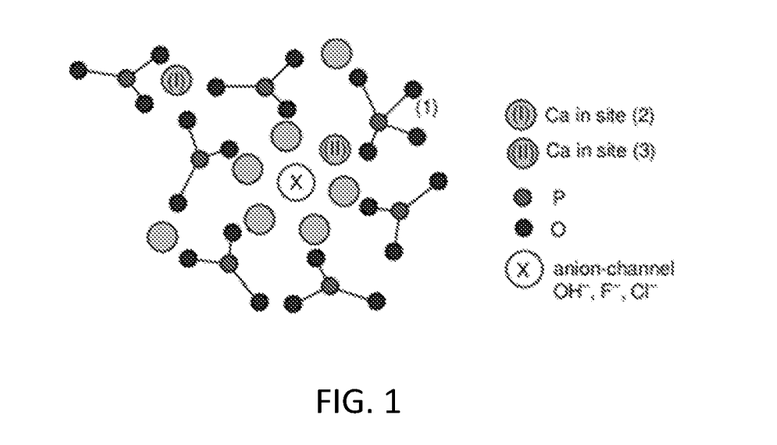
FIG. 1 is a chemical representation of hydroxyapatite.

It is known that hydroxyapatite is basically the core minerals of calcium and phosphate that compose the hard structures and inorganic make up of tooth, bone and dentin as shown in FIG. 1. Hydroxyapatite is a naturally occurring form of the mineral calcium apatite (calcium, phosphorous, and oxygen) that grows in hexagonal crystals. Pure hydroxyapatite is white in color. It makes up most of the human bone structure and builds tooth enamel. It is essentially composed of calcium and phosphorus ions and oxygen that work synergistically to get calcium at the interface level where it is needed. So, if there is a deficiency in calcium at that area the phosphorus is key to opening up the pathways for the body to absorb and use the calcium mineral in its calcification or hardening or re-mineralization.

Figure 2:
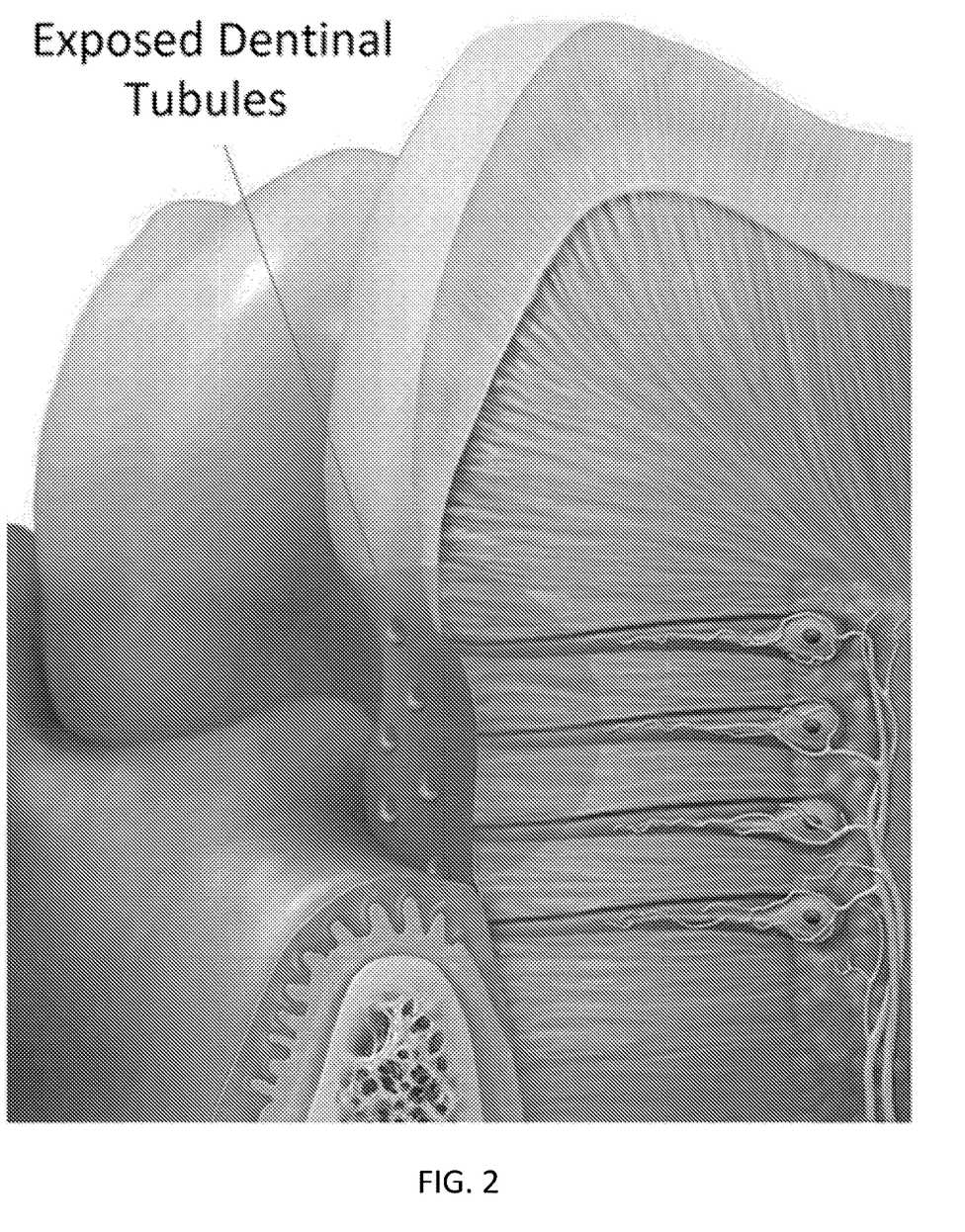
FIG. 2 is sectional diagram of a person's tooth now showing the exposed dentinal tubules.
Figure 3:
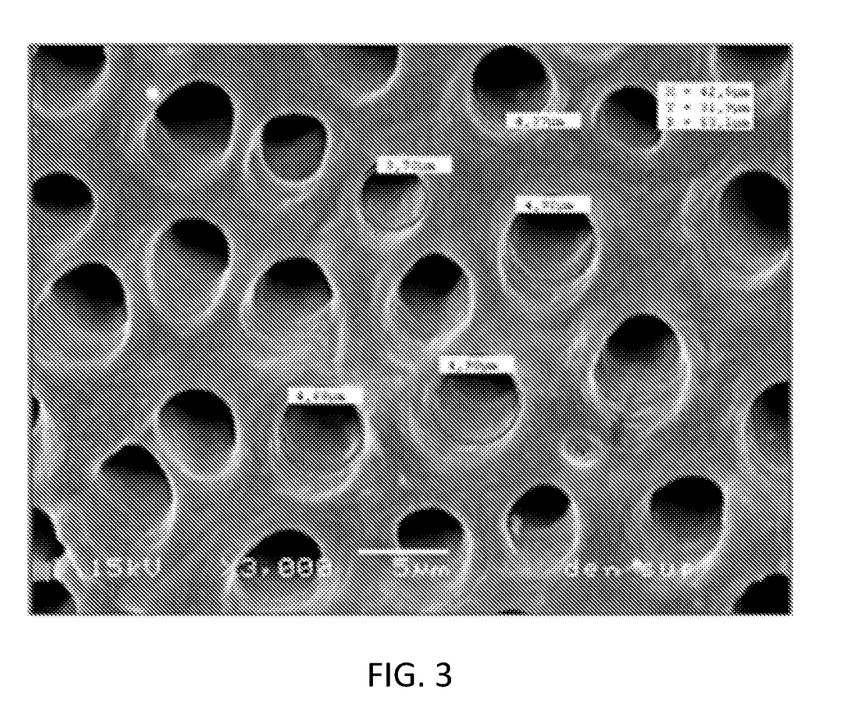
FIG. 3 is a picture of an SEM micrograph showing dentinal tubules in bovine dentin.

The hydroxyapatite can come in many forms, but by using it as a small molecule nano particle the research shows it can be absorbed right into the surface opening inside the dentinal tubules as shown in FIG. 2. The dentinal tubules are those areas within the dentin complex that communicates outward from the pulp or nerve. It communicates from the inside of the tooth outward to hydrate the tooth all the way through the dentin and just shy of the enamel. Therefore, the dentinal tubules complex are structurally inorganic and the surrounding area is composed of an extratubular organic complex. The dentinal tubules have a certain average circumference which is too small for large molecule hydroxyapatite to easily get inside the tubule. FIG. 3 is an SEM micrograph showing dentinal tubules and total area measured under in bovine dentin.

When a patient feels toothache pain it is because essentially from the cavity causing bacteria that has eaten through the enamel and touched one of the tubules. Thus the consequent hydraulic pressure that it forces against the newly exposed open tubule may hydraulically communicate down through the tubule to stimulate the pulp or nerve of the tooth. This is not unlike an experiment, if you fill a straw up with water you can put your finger on each hand end tap one side or the other and feel the pulse all the way through. What the nano-hydroxyapatite can do is penetrate the external aspect of the dental tubule and seed itself in the opening, thereby pulling the calcium with the phosphoric ions into the area to effectively occlude those openings. This action will seal the tubules and prevent the communication of nerve response and transmission.

The present invention's nano-hydroxyapatite contain particles of 50 nanometers, not microns! 1 micron corresponds to 1000 nanometers. So, 50 nanometers are 0.05 microns, which means that on average the particles of the present invention are about 40× smaller than the diameter of a dentine tubule (~2 microns, i.e. 2000 nanometers) and therefore easy to penetrate and occlude the tubules.

The following articles are incorporated in full herein with this reference: https://fluidinova.com/docs/nanoxim_carepaste_tds.pdf and https://www.sciencedirect.com/topics/engineering/peritubular-dentin.

Independent studies of hydroxyapatite can show a decrease in sensitivity for people that have sensitive teeth so this disclosure will now help in the re-mineralizing aspect of dentinal enamel.

The development of the toothpaste has been ongoing since quite some time as the inventor has at first attempted to combine a reductive side with an oxidative side and mix the two through a dual tube system. This also would include on the oxidative side adding those ozonides or ozone that has been captured in an olive oil or grapeseed oil as they have the greatest number of potential bonds to hold the ozone in place.

The problem the inventor discovered is that in order to get the ozone to stay stable within the olive oil or grapeseed oil, it is extremely difficult as the process of putting ozone in oil oxidizes the oil and creates a sort of slow rancidity to the oil. This is less than ideal and systems were being looked at to try to eliminate or lessen the rancidity. These attempts were not successful and further research shows that when the ozone is gassed into the olive oil or grapeseed oil it breaks down into what is called ozonides. These ozonides break down into many different independent smaller compounds, namely varying types of aldehydes. The problem is one of the aldehydes happens to turn out to be formaldehyde. The inventor did not want to have a toothpaste that harbored any type of these aldehydes or formaldehyde. These were some of the things that the inventor learned overtime with research and experimentation.

Further, most of the aldehydes are a reactive species, therefore, they are generally toxic to the body. Aldehydes have been reported to have cytotoxic, mutagenic, genotoxic and carcinogenic effects. (See Lindahl 1992. Apr. 22, 2019)

In the field of endodontics, most of the problems of endodontic origin have a bacterial etiological agent. Thus, there is a continued interest in seeking more effective chemical substances that can replace the camphorated paramonochlorophenol or antibiotics as intracanal medicaments. Among the possible substances, ozone has some interesting biological characteristics such as: bactericidal action, debriding effect, angiogenesis stimulation capacity and high oxidizing power. The purpose of this study was to chemically evaluate the presence of ozone in sunflower, castor, olive and almond oil, as well as in propylene glycol and byproducts of ozonation, such as formaldehyde. These compounds were ozonized, inserted into empty and sterile vials, and analyzed by testing the reaction between ozone and indigo, for determining the presence of ozone, and subjected to the chromotropic acid test for determining the presence of formaldehyde. It was observed complete absence of ozone in all samples tested and presence of formaldehyde. The bactericidal and healing action of ozonized oils could be attributed to products formed by the ozonation of mineral oils, such as formaldehyde, not to the ozone itself.

Formaldehyde may be present as a byproduct of lipid and ozone reaction. As formaldehyde is a considerable toxic product and also can interfere with cellular integrity, the evaluation of the presence of formaldehyde has become mandatory. The reaction between formaldehyde and chromotropic acid heated in a solution with concentrated sulfuric acid results in a solution with violet color, indicating the presence of formaldehyde. In the test performed, all samples became violet, showing the presence of formaldehyde in all samples after ozonation.

Propylene glycol was used as control in this study because it is a substance widely used in endodontics as a vehicle for intracanal medication and due to the lack of antimicrobial power.

The healing power of the substances evaluated in the present study could be attributed to the ozonized products formed, such as the formaldehyde produced after ozonation, and not the ozone itself. It is noteworthy that some issues on the effect of ozone therapy on the microbiota should be further elucidated, such as the optimal concentration, the penetration of the compound into the dentinal tubules and the ideal application time.

Therefore, this newer additional patent application incorporates many of these principles we have learned—which it is now a trio approach. Now, the inventor wants to safely eliminate the harmful pathogenic bacteria, but then also wants a way to backfill the good bacteria to then aid in remineralizing teeth and increasing gingival health. The nano-hydroxyapatite shows a mild whitening effect as it lays down minerals and grows a white crystalline surface. The advanced oral probiotics does the backfilling aspect quite nicely and that has many independent studies to back up how that creates an affective homeostasis in the oral milieu.

With the advanced oral probiotics we have made some slight modifications. Mainly the inventor has slightly reduced the amount of dicalcium phosphate as it was too "chalky" which was creating too much of a drying effect in the mouth itself. Therefore, it is lessened. The inventor has also brought the percentages from 30 mg's to 5 mg's. We also decided to slightly lessen the percentage of zinc in the formula, from 2 mg's per tablet to 0.5 mg's. The inventor wanted to make this formula available for those that were suffering from any type of ear nose or sore throat as a nutritional supplement to help bring faster bacterial balance and homeostasis to those areas. Based on research, published literature and observation in those cases that were suffering with ear, nose, or throat infection, studies of our individual strains show that they can do just that, reduce the incidence, severity, and longevity of said ear, nose and throat infections inclusive of strep throat. Therefore, if someone was taking seven or eight or even 10 lozenges per day we wanted to make sure the dose of zinc would stay well within the RDA and not potentially cause any of the other-wise unwanted transient symptoms of loss of smell or taste as was observed in high dose cold remedy zinc lozenges from other manufacturers (not from the inventor).

The toothpaste that I formulated has been perfected and we have the base formula which now comes in at a pH of 7.1 to 7.4 which is ideal. The closer we could keep it to 7.0 was more ideal as that brings about greater health and balance to the mouth.

The tea tree oil is at a 0.2% dose for maximum effectiveness. All our research and studies indicate that tea tree oil at 0.2% even sometimes slightly less were found to be highly efficacious in handling the many types of pathogenic bacteria associated with oral disease. The mixing instructions are very specific in how we mix the product together. The powdered portions have to be mixed first and then the essential oils are added at the end to create a homogenous mix. It has to be mixed beyond the regular manufacture timeframe to fully incorporate the volatile oils within the homogenous mix. Then it must sit in the vat for a period of time up to 24 hours for it to outgas any excess volatile essential oils. By doing the outgas steps correctly and letting the formula further balance out, this would bring the pH closer to 7.1 to 7.5. The consistency of the toothpaste itself brings about an extremely low RDA (Relative Dentin Abrasivity). It took many attempts to formulate and perfect this toothpaste gel free of glycerin. This is a major part of our research and data that was performed to bring about a superior product with low abrasiveness and with low destruction to the surface of enamel with normal brushing.

The inventor further discovered (and resolved) the challenge that by not putting glycerin in the formula, it made it difficult to prevent bacteria from growing. The inventor overcame that by adding the tea tree oil and also by decreasing the water content and slightly increasing the essential oil flavoring factor. The inventor also added a natural preservative to further aid in passable preservative efficacy testing (PET). This added ingredient for preservation is certified organic citrus extract that contains active bioflavonoids for preservation and antimicrobial activities. This Biosecur® product is designed exclusively for use by manufacturers of functional blends with antimicrobial and/or preservative properties.

All the ingredients are of a natural and or organic relationship with the exception of the nano-hydroxyapaite which has to be processed synthetically but is essentially calcium and phosphorus ion chemistry.

The OraRestore essential oils, tooth and gum tonic can be used as a mouthwash and also as an additive to toothpaste, or just with one or two drops on a toothbrush or on a fingertip and rubbing, or brushing it inside one's mouth around the teeth and gums to bring about increased fresh breath and decreased pathogenic bacterial load within the mouth. One can also use it as a mouthwash by adding 6 drops to a ½ glass of water and gargle and swish for maximum healthy teeth and gums and fresh breath. The formula is enclosed and it satisfies the reductive side of the original patent thereby bringing a true antioxidant enhanced product into the mouth. The OraRestore essential oils for the teeth and gums was developed in response to the many requests we got from our beta testing and feedback from our customers on the efficacy of the advanced oral probiotics. The inventor was getting rave reviews on the oral probiotics all the way from decreased bleeding and anecdotal reports of increased gum health, (including many favorable reports from hygienist and dentist who used the Advanced Oral Probiotics on their patients). Also reported was fresher, cleaner teeth, healthier gums and fresher breath, less plaque/tartar sticking to the teeth, (all these things theoretically are shown in the research but also prove out anecdotally).

However, the one thing our customer base and patients requested was for something which could be more immediate as the probiotics are a lifestyle change and can take anywhere from days to months to get a positive result from their use. So I developed the OraRestore essential oil to satisfy the immediate handling to bring about healthier gums and fresher breath while the probiotics would be working for long-term improvement. Further, I wanted a formula that could be antioxidant and also suppress the pathogenic bacterial simultaneously as is shown in our clinical studies. What I discovered was that those beta tested with the OraRestore oils liked the immediate gratification gained because their gums felt so much tighter and healthier and their family members and friends commented on the fact that they had much fresher breath.

The formula taught herein has spearmint and tea tree oils and a base of sweet almond oil combine with an all-natural flavoring to reduce the overall bitterness of the product. Even that part of the formula has been revealed in this patent application. Being an essential oil based product this satisfies the antioxidant side of our patent and delivers an age old application of essential oil anti-bacterial application. This satisfies the trio delivery system of this application.

The goal with the toothpaste was to help bring greater health to people's teeth and gums and overall oral health. Ideally what we wanted was a toothpaste that was not abrasive and could super clean the teeth so it felt just like they just left the dentist office after they had that polished hygiene cleaned feeling on their teeth. The problem is the product that we use in the dentist office could not be used every day as it is a bit too abrasive long-term. The inventor's product will also clean the teeth, provide a super clean feeling even afterwards because what I have developed is a glycerin free product. Apparently the glycerin is negative charge and plaque bacteria is positive charge, so therefore when you have a glycerin toothpaste (which is 99.9% of all toothpastes) the teeth will feel dirty within 10-20 minutes. Versus our product which is 99.9% glycerin free and makes the teeth feel slick and clean because there's no glycerin left over coating the teeth, thus eliminating the glycerine-plaque magnet. Furthermore, the product of the present invention super coats the teeth with the nano-hydroxyapatite which works immediately to help re-mineralize the teeth, decreasing sensitivity and increasing dental health. The inventor also knows the nano-hydroxyapatite lays down a white microcrystalline layer and micro remineralize the enamels while it occludes, seals and protects any open dentinal tubules while laying down new crystalline formations. Also, the present invention product being 99.9% glycerine free does not elicited the deleterious effects of glycerine based toothpaste products, because glycerin can act as a barrier to the normal mineralization sequence in the otherwise healthy mouth, and thus act as an inhibiting agent for the mouth's natural buffering agents. Research is showing it can take 10 to 18 vigorous swishes to get glycerin off the surface of the teeth depending on viscosity and concentration. Sadly, the "glycerine effect" is not well known in the dental industry and therefore it is a unique aspect of the present invention formulation and trio of products to be 99.9% free of glycerine.

Again the trio of my products is meant to reduce the harmful bacteria naturally with essential oils and various other ingredients which are listed in my formulation and to minimize creating a bacteria resistant response, which thankfully I have not seen with using essential oils. And by the way, essential oils go back for thousands of years as treatments when there were various infections and ailments plaguing the body, but now are being applied to the teeth for the first time.

This trio of ingredients is formulated to: (1) reduce the harmful bacteria in the mouth; (2) put back the healthy bacteria in the mouth (98% of the population has the bacteria that can cause gum disease and cavities. If they have super hard and strong enamel they can resist decay and gum disease. If they brush and floss well they can break up the microbiome and various bacterial strains that causes gum disease and cavities. However, if they are lacking in those skills or they have a huge joy of eating carbohydrate rich and sugar rich foods they increase the risk of dental diseases.); and (3) rebuild teeth and strengthen gingiva.

By reducing the amount of sugar intake and increasing the hygiene practices of brushing, flossing and seeing the dentist once a year and by using the trio of oral care products as outlined above, we can naturally reduce the pathogenic bacteria and then put in the healthy bacteria. By putting in the healthy bacteria it brings the 98% of our population that doesn't have the high numbers of healthy bacteria closer to the 2% population that appears to be immune to gum disease and tooth decay. We also discovered through various research articles that 2% of the population does not get decay or gum disease and they are loaded with a huge number of the types of bacteria that we have in the advanced oral probiotic formulation. So part of the trio approach is killing the bad bacteria and then putting back in the good bacteria. If we can bring about homeostasis and balance to the mouth with the good bacteria, decrease the sugar and carbohydrate consumption and increase the flossing and brushing habits of patients we can make an effective dent in the pandemic in this world as labeled by the US Surgeon General gum disease and cavities, are a worldwide pandemic.

The goal is to help reduce the bad bacteria with the trio of ingredients. The third part of the formulation is the toothpaste. Using the glycerin free nano-hydroxyapatite toothpaste formula with antioxidants and tea tree oil further cleans the teeth, mouth and gums and also to helps to remineralize the structure of the teeth and the inner portion of the tooth known as the dentin. This trio application of products works best if coupled with daily mechanical aids such as brushing and flossing. At home and as part of one's diet, striving to decrease sugar consumption and refined carbohydrates and excess fruits. There are multiple ways to use the (OraRestore) essential oil's liquid drops, for example add 1 drop to the toothpaste, or 6 drops to ½ cup of water as a mouthwash, or 1 drop on your clean finger and rub it into your teeth and gums, or a small amount on the floss to really increase interproximal dental health and freshness.

Now one can then add back beneficial bacteria to this clean slate by using the Advanced Oral Probiotics because we have greatly reduced the pathogenic bacteria thus creating room for the daily application of beneficial bacteria strains. By using this product as a trio you first reduce the harmful bacteria and then using the advanced oral probiotics you put back in the beneficial bacteria. By using the tooth oils and toothpaste with brushing and flossing just before using the Advanced Oral Probiotics you are greatly assisting the body in remineralizing the enamel by taking the probiotic lozenge you continue that affect actually long-term by holding it in the mouth as the dicalcium phosphate further breaks down into hydroxyapatite.

One would not use the trio of products in the reverse order, namely taking the advanced probiotic first and then cleansing the mouth with toothpaste and/or the tonic/oil whether alone or in combination. If done backwards, this would negate the long-term affect created by the lozenge to impart beneficial bacteria into the oral cavity and would further negate the assistance the probiotic would give to remineralizing the enamel, so it's very important that it's used in the correct order, which is: (1) first, using the OraRestore oil's/brushing/rubbing/rinsing/applying to floss;

(2) next, using the toothpaste; and (3) lastly, covering/ seeding/backfilling the now cleaned environment with the advanced oral probiotic lozenge.

In the product there may be various filler ingredients, such as excipients and GMO free corn and the like.

All the excipients are GRAS and are used to allow us to compress the ingredients (binding agents) into tablet form and also provide shelf-life stability for the probiotic organisms.

Isomalt is a sugar substitute, a type of sugar alcohol, used primarily for its sugar-like physical properties. It has only a small impact on blood sugar levels and does not promote tooth decay. It is used as a primary binding agent and lends some sweetness to the chewable formulation. In addition, this ingredient has a low water activity level, which does not negatively impact the shelf-life stability of the probiotic organisms.

Inulin is a naturally occurring polysaccharide that serves as a prebiotic, or food source, for the probiotic organisms. This ingredient is derived from chicory root, which is well known for its toxicity to internal parasites. This ingredient also helps humans with weight loss, constipation, improved bowel function and overall general health.

Microcrystalline Cellulose is the primary bulking/binding agent used in tablet manufacturing. It is a naturally occurring polymer, so it is ideal as a tablet excipient.

Glyceryl behenate is mainly used as a tablet and capsule lubricant and as a lubricant in oral solid dosage formulations. This ingredient prevents the powder from sticking to the tablet presses.

Dicalcium phosphate is used as a tableting agent in some pharmaceutical and nutraceutical preparations to improve the hardness of the tablet. It is also used in some toothpastes as a tartar control agent.

Flavor excipients and *Stevia* are used to improve the taste profile of the nutraceutical tablets.

Now in more detail, there is a preferred method of creating the toothpaste, which is taught herein in phases as Phase A, B, C and D. In Phase A, one first creates the aloe base by begin incorporating the natural preservatives to wet and activate at the start. In Phase B, one then slowly introduces the powders including the nano-hydroxyapatite, zeodent silicates and calcium carbonate plus sweeteners. This specific mixing schedule allows the proper integration of essential oils and prevent over activation of the natural surfactant. By mixing this way it stabilizes the ingredients and allows the formula to mix effectively and it allows time for proper absorption and stability.

Phase A (weigh and add the ingredients one by one and mix on medium speed for 20 minutes):

| Water | 30.79% by mass |
|---|---|
| Aloe Barbadensis Powder, Organic | 00.08% by mass |
| Himalayan Pink Salt | 02.00% by mass |
| Natural Preservative (Biosecur® C320C) | 00.10% by mass |
| Citric Acid | 00.40% by mass |
| Xylitol | 30.00% by mass |
| Ascorbic Acid (Vitamin C) | 00.10% by mass |

Phase B (weigh and add the powders and mix at a faster speed and allow them to blend in for 20 minutes):

| Baking Soda | 02.50% by mass |
|---|---|
| Zinc Gluconate | 00.20% by mass |
| Zinc Citrate | 01.00% by mass |
| Calcium Carbonate | 10.00% by mass |
| Calcium Carbonate in Hydroxyapatite Shell (Omyadent® 100-OG) | 05.00% by mass |
| Silicon Dioxide, Precipitated (Zeodent® 165) | 05.00% by mass |
| Glycyrrhizic Acid (Magnasweet® 100) | 03.00% by mass |
| Hydroxyapatite (HAp) - Acicular Powder | 06.50% by mass |
| sodium bentonite (Polargel® NF) | 01.00% by mass |

Phase C (pre-mix phase C ingredients and then add to main mix, mixing at high speed for 25 minutes):

| Vitamin E Oil (Clear) | 00.10% by mass |
|---|---|
| Tea Tree Oil | 00.20% by mass |
| Wintergreen Oil | 02.50% by mass |
| Cellulose Gum (high viscosity) | 01.00% by mass |

Phase D (weigh and add the surfactant and mix this time at a slow speed so that it integrates without creating foam for 15 minutes):
Sodium Cocoyl Glutamate 01.50% by mass All of the ingredients taught above can be in a range of plus or minus 20% from their listed percentage of mass.

Some of the more important ingredients of the toothpaste are the aloe, nano-hydroxyapatite, xylitol, tea tree and silicates. The aloe greatly aids in gingival health. The nano-hydroxyapatite promotes a remineralization process that happens in the oral cavity. The xylitol acts like a Trojan horse and fools the bacteria associated with cavities to try to break them down as their energy source, but the bacteria lacks the ability to do so and instead fatigues and dies in the attempt thus reducing the bacteria associated with tooth decay. The tea tree oil is antibacterial and is highly effective in reducing the pathogenic bacteria that cause gingivitis and gum disease. The delicate balance of the silicates (silicon dioxide) will very mildly cleanse the tooth surface including the orifice of the dentinal tubules which are key in creating a clean surface. The method of the present invention cleanses and disinfects the dentinal tubule, where then the silicates can then seed the area with calcium, phosphorus and oxygen. This creates a more susceptible surface area to allow the rapid incorporation of calcium ions into the otherwise organically occluded bacteria contaminated tubule interface. By cleansing first, it creates a clean debrided surface and accentuates rapid crystal formation.

Furthermore, the following ranges are acceptable of these key ingredients: tea tree 00.10-01.00% by mass; nano-hydroxyapatite 05.00-20.00% by mass; aloe water 05.00-37% by mass; xylitol 05.00-40.00% by mass.

Now turning to the tonic, the tonic comprises the following ingredients, which is normally distributed in a 15 ml bottle:

| Tea Tree Essential Oil | 0.2% by mass |
|---|---|
| Peppermint Essential Oil | 47% by mass (7 ml) |
| Spearmint Essential Oil | 20% by mass (3 ml) |
| Sweet Almond Vegetable Oil | 33% by mass (5 ml) |

The peppermint and spearmint essential oil together may comprise 20-50% by mass. The almond essential oil may comprise 15-35% by mass. The tea tree essential oil may comprise 00.10-01.00% by mass.

The tonic is a synergistic formula, where the combination of essential oils regulate one another's effect such that they all act as carriers of each other and can greatly increase any one individual oil. The inventor's OraRestore oils study shows the formula can reduce the predominant *Streptococcus* strains associated with dental caries, but not to a point that interferes with the nitric oxide (NO) creating benefits of these *Streptococcus* strains. Sadly, new research is showing frequent use of other (not the inventor's products) medicinal mouth washes totally wipe out the beneficial aspects of the *Streptococcus* strains resulting in hypertension in frequent users. The inventor's formula does not create this deleterious effect. This is due to the synergistic formula effect and its ability to target mainly pathogenic bacteria and fungus and only mildly suppress the beneficial species.

In the claims, it may recite an ingredient percentage that then has an associated variation percentage. The variation percentage is that of the ingredient percentage and not an overall variation of the formulation such as the toothpaste or tonic. For example, the toothpaste describes a baking soda ingredient of 2.50% by mass of the toothpaste. This then means the variation is plus or minus 20% of the 2.5%, such that the baking soda may vary between 2 and 3%.

See also: "Ozonized Oils: A qualitative and quantitative analysis" by Adriana Simionatto Guinesi, Carolina Andolfatto, Idomeo Bonetti-Filho and Arnaldo Cardoso, January 2011Brazilian Dental Journal 22(1):37-40, DOI:10.1590/S0103-64402011000100006. (https://www.researchgate.net/publication/51076588_Ozonized_Oils_A_qualitative_and_quantitative_analysis)

See also: "Comparative study of tubular diameter and quantity for human and bovine dentin at different depths" by Murilo Baena Lopes, Mário Alexandre Coelho Sinhoreti and Alcides Gonini Júnior, January 2009, Brazilian Dental Journal 20(4):279-83, DOI:10.1590/S0103-64402009000400003. (https://www.researchgate.net/publication/41001865_Comparative_study_of_tubular_diameter_and_quantity_for_human_and_bovine_dentin_at_different_depths)

See also: "Isolation and Preparation of Nanoscale Bioapatites from Natural Sources: A Review" by Monika Supová, April 2014, Journal of Nanoscience and Nanotechnology 14(1):546-63, DOI:10.1166/jnn.2014.8895. (https://pubmed.ncbi.nlm.nih.gov/24730282/)

Although several embodiments have been described in detail for purposes of illustration, various modifications may be made to each without departing from the scope and spirit of the invention. Accordingly, the invention is not to be limited, except as by the appended claims.

What is claimed is:

1. A method of cleaning a user's teeth and/or gums, the method comprising the steps of:
   a) applying a tonic to the user's teeth and/or gums by either brushing, rubbing, rinsing and/or flossing with the tonic, the tonic comprising:
      tea tree essential oil comprising 0.10-1.0% by mass of the tonic;
      peppermint and spearmint essential oil comprising 20.0-50.0% by mass of the tonic;
      almond essential oil comprising 15.0-35.0% by mass of the tonic;
   b) brushing with a toothpaste, the toothpaste comprising:
      aloe comprising 5.0-37.0% by mass of the toothpaste;
      xylitol comprising 5.0-40.0% by mass of the toothpaste;
      silicon dioxide comprising 3.0-12.0% by mass of the toothpaste;
      tea tree essential oil comprising 0.10-1.0% by mass of the toothpaste;
      nano-hydroxyapatite comprising 3.0-40.0% by mass of the toothpaste, wherein the nano-hydroxyapatite consists essentially of particles of 50 nanometers (0.05 microns) or smaller; and
   c) seeding the user's teeth and gums with an oral probiotic, the oral probiotic being in the form of a tablet, the oral probiotic tablet comprising:
      i.) *Lactobacillus acidophilus* comprising 15.0% to 40.0% per mass of the oral probiotic;
      ii.) *Lactobacillus reuteri* comprising 5.0% to 20.0% per mass of the oral probiotic;
      iii.) *Lactobacillus salivarius* comprising 5.0% to 20.0% per mass of the oral probiotic;
      iv.) *Lactobacillus paracasei* comprising 5.0% to 20.0% per mass of the oral probiotic;
      v.) *Streptococcus* thermophiles comprising 5.0% to 20.0% per mass of the oral probiotic;
      vi.) *Streptococcus salivarius* K-12 comprising 5.0% to 30.0% per mass of the oral probiotic;
      vii.) *Streptococcus salivarius* M-18 comprising 5.0% to 30.0% per mass of the oral probiotic;
      viii.) zinc oxide comprising 0.2% to 5.0% per mass of the oral probiotic;
      ix.) hydroxyapatite comprising 0.1% to 25.0% per mass of the oral probiotic; and
      x.) dicalcium phosphate comprising 0.1% to 5.0% per mass of the oral probiotic;
   d) wherein step c) must come after both step a) and step b).

2. The method of claim 1, wherein step a) is before step b).

3. The method of claim 1, wherein step b) is before step a).

4. The method of claim 1, wherein step a) and step b) are at the same time.

5. The method of claim 1, wherein the tonic has a pH of 7.1 to 7.4.

6. The method of claim 1, wherein the toothpaste has a pH of 7.1 to 7.4.

7. The method of claim 1, wherein the tonic is 99.9% by mass free of glycerin.

8. The method of claim 1, wherein the toothpaste is 99.9% by mass free of glycerin.

9. A method of cleaning a user's teeth and/or gums, the method comprising the steps of:
   a) applying a tonic to the user's teeth and/or gums by either brushing, rubbing, rinsing and/or flossing with the tonic, the tonic comprising:
      tea tree essential oil comprising 0.10-1.0% by mass of the tonic;
      peppermint and spearmint essential oil comprising 20.0-50.0% by mass of the tonic;
      almond essential oil comprising 15.0-35.0% by mass of the tonic;
   b) brushing with a toothpaste, the toothpaste comprising:
      aloe comprising 5.0-37.0% by mass of the toothpaste;
      himalayan pink salt comprising 2.0-5.0% by mass of the toothpaste;
      natural preservative comprising 0.10-2.0% by mass of the toothpaste;
      citric acid comprising 00.40% by mass of the toothpaste with a variation of plus or minus 20% of the base value;
      xylitol comprising 30.0-50.0% by mass of the toothpaste;

ascorbic acid comprising 00.10% by mass of the toothpaste with a variation of plus or minus 20% of the base value;
baking soda comprising 02.50-10.0% by mass of the toothpaste;
zinc gluconate comprising 0.20-2.0% by mass of the toothpaste;
zinc citrate comprising 01.00% by mass of the toothpaste with a variation of plus or minus 20% of the base value;
calcium carbonate comprising 10.00% by mass of the toothpaste with a variation of plus or minus 20% of the base value;
calcium carbonate in a hydroxyapatite shell comprising 05.00% by mass of the toothpaste with a variation of plus or minus 20% of the base value;
silicon dioxide comprising 5.0-15.0% by mass of the toothpaste;
glycyrrhizic acid 3.0-6.0% by mass of the toothpaste with a variation of plus or minus 20% of the base value;
nano-hydroxyapatite comprising 6.50-20.0% by mass of the toothpaste, wherein the nano-hydroxyapatite consists essentially of particles of 50 nanometers (0.05 microns) or smaller;
sodium bentonite comprising 1.0-3.0% by mass of the toothpaste;
vitamin E oil comprising 0.10-3.0% by mass of the toothpaste;
tea tree oil comprising 0.10-3.0% by mass of the toothpaste;
wintergreen oil comprising 1.0-3.0% by mass of the toothpaste;
cellulose gum comprising 1.0-3.0% by mass of the toothpaste;
sodium cocoyl glutamate comprising 1.0-4.0% by mass of the toothpaste;
c) seeding the user's teeth and gums with an oral probiotic, the oral probiotic being in the form of a tablet, the oral probiotic tablet comprising:
i) *Lactobacillus acidophilus* comprising 15.0% to 40.0% per mass of the oral probiotic;
ii) *Lactobacillus reuteri* comprising 5.0% to 20.0% per mass of the oral probiotic;
iii.) *Lactobacillus salivarius* comprising 5.0% to 20.0% per mass of the oral probiotic;
iv.) *Lactobacillus paracasei* comprising 5.0% to 20.0% per mass of the oral probiotic;
v.) *Streptococcus* thermophiles comprising 5.0% to 20.0% per mass of the oral probiotic;
vi) *Streptococcus salivarius* K-12 comprising 5.0% to 30.0% per mass of the oral probiotic;
vii) *Streptococcus salivarius* M-18 comprising 5.0% to 30.0% per mass of the oral probiotic;
viii.) zinc oxide comprising 0.2% to 5.0% per mass of the oral probiotic;
ix.) hydroxyapatite comprising 0.1% to 25.0% per mass of the oral probiotic; and
x.) dicalcium phosphate comprising 0.1% to 5.0% per mass of the oral probiotic;
d) wherein step c) must come after both step a) and step b).

10. The method of claim 9, wherein step a) is before step b).

11. The method of claim 9, wherein step b) is before step a).

12. The method of claim 9, wherein step a) and step b) are at the same time.

13. The method of claim 9, wherein the tonic has a pH of 7.1 to 7.4.

14. The method of claim 9, wherein the toothpaste has a pH of 7.1 to 7.4.

15. The method of claim 9, wherein the tonic is 99.9% by mass free of glycerin.

16. The method of claim 9, wherein the toothpaste is 99.9% by mass free of glycerin.

17. A method of producing a toothpaste, the method comprising the steps of:
a) mixing the following ingredients into a first mixture:
aloe comprising 5.0-37.0% by mass of the toothpaste;
himalayan pink salt comprising 2.0-5.0% by mass of the toothpaste;
natural preservative comprising 0.10-2.0% by mass of the toothpaste;
citric acid comprising 00.40% by mass of the toothpaste with a variation of plus or minus 20% of the base value;
xylitol comprising 30.0-50.0% by mass of the toothpaste;
ascorbic acid comprising 00.10% by mass of the toothpaste with a variation of plus or minus 20% of the base value;
b) mixing the first mixture with the following ingredients forming a second mixture:
baking soda comprising 02.50-10.0% by mass of the toothpaste;
zinc gluconate comprising 0.20-2.0% by mass of the toothpaste;
zinc citrate comprising 01.00% by mass of the toothpaste with a variation of plus or minus 20% of the base value;
calcium carbonate comprising 10.00% by mass of the toothpaste with a variation of plus or minus 20% of the base value;
calcium carbonate in a hydroxyapatite shell comprising 05.00% by mass of the toothpaste with a variation of plus or minus 20% of the base value;
silicon dioxide comprising 5.0-15.0% by mass of the toothpaste;
glycyrrhizic acid 3.0-6.0% by mass of the toothpaste with a variation of plus or minus 20% of the base value;
nano-hydroxyapatite comprising 6.50-20.0% by mass of the toothpaste, wherein the nano-hydroxyapatite consists essentially of particles of 50 nanometers (0.05 microns) or smaller;
sodium bentonite comprising 1.0-3.0% by mass of the toothpaste;
c) mixing the second mixture with the following ingredients forming a third mixture:
vitamin E oil comprising 0.10-3.0% by mass of the toothpaste;
tea tree oil comprising 0.10-3.0% by mass of the toothpaste;
wintergreen oil comprising 1.0-3.0% by mass of the toothpaste;
cellulose gum comprising 1.0-3.0% by mass of the toothpaste;
d) mixing the third mixture with the following ingredient forming the toothpaste:
sodium cocoyl glutamate comprising 1.0-4.0% by mass of the toothpaste.

18. The method of claim 17, wherein the toothpaste has a pH of 7.1 to 7.4.

19. The method of claim 17, wherein the toothpaste is 99.9% by mass free of glycerin.

* * * * *

UNITED STATES PATENT AND TRADEMARK OFFICE
CERTIFICATE OF CORRECTION

PATENT NO. : 11,564,878 B2
APPLICATION NO. : 17/303780
DATED : January 31, 2023
INVENTOR(S) : Paul O'Malley It is certified that error appears in the above-identified patent and that said Letters Patent is hereby corrected as shown below:

In the Claims

Column 13, Claim 9, Line 42, "i)" should read --i.--.

Column 13, Claim 9, Line 44, "ii)" should read --ii.--.

Column 13, Claim 9, Line 52, "vi)" should read --vi.--.

Column 13, Claim 9, Line 54, "vii)" should read --vii.--.

Signed and Sealed this
Twenty-first Day of March, 2023

Katherine Kelly Vidal
*Director of the United States Patent and Trademark Office*